United States Patent [19]

Yamamoto et al.

[11] Patent Number: 4,856,504
[45] Date of Patent: Aug. 15, 1989

[54] ANTIMICROBIAL WOUND DRESSING AND SKIN FIXATOR FOR ORTHOPEDIC PINS

[75] Inventors: Ronald Yamamoto; Stanley R. Conston, both of Redwood City; Sophia Pesotchinsky, Palo Alto, all of Calif.

[73] Assignee: Vitaphore Corp., Menlo Park, Calif.

[21] Appl. No.: 108,515

[22] Filed: Oct. 15, 1987

[51] Int. Cl.$^4$ ............................................. A61F 5/04
[52] U.S. Cl. ........................... 128/92 ZW; 128/92 Z; 128/640; 128/DIG. 26; 128/888; 604/180
[58] Field of Search ............... 128/155, 156, 132 R, 128/154, 42 Z, 92 ZW, 92 YR, 92 VW, 92 VD, 92 V, 84 C, 82, 82 B, 334, 640, 92 R, DIG. 26, 888; 604/304, 305, 306, 307, 346, 355, 336, 174, 175, 179, 180; 433/172

[56] References Cited

U.S. PATENT DOCUMENTS

| | | | |
|---|---|---|---|
| 3,234,941 | 2/1966 | Tucker | 128/888 |
| 3,286,713 | 11/1966 | Kurtz et al. | 128/156 |
| 3,683,911 | 8/1972 | McCormick | 128/DIG. 26 |
| 3,957,048 | 5/1976 | Jacobs | 604/180 |
| 4,342,309 | 8/1982 | Eftekhar | 128/92 VD |
| 4,392,857 | 7/1983 | Beron | 128/DIG. 26 |
| 4,516,968 | 5/1985 | Marshall et al. | 128/DIG. 26 |
| 4,579,120 | 4/1986 | MacGregor | 604/180 |
| 4,632,671 | 12/1986 | Dalton | 604/174 |
| 4,675,006 | 6/1987 | Hrushesky | 604/180 |
| 4,685,455 | 8/1987 | Vrouenroets | 128/156 |

FOREIGN PATENT DOCUMENTS 2035096 6/1980 United Kingdom ................ 604/180

Primary Examiner—Richard J. Apley
Assistant Examiner—Paul Prebilic
Attorney, Agent, or Firm—Flehr, Hohbach, Test, Albritton & Herbert

[57] ABSTRACT

An antimicrobial orthopedic pin percutaneous protection kit is provided comprising a shield and a pad and patch combination. The shield comprises a central elastomeric collar having a longitudinal orifice and having one end of the collar substantially orthogonally disposed to an elastomeric peripheral flange, the flange extending around the end of the collar, with a radial slit extending through the collar and flange from the longitudinal orifice of the collar to the outer edge of the flange. The shield is adapted with a means for securing the collar around an orthopedic pin to prevent longitudinal motion of the pin. The patch contains an antimicrobial agent and is centrally attached to a porous pad. The pad and patch have a pressure-sensitive adhesive coating on the exposed surfaces.

14 Claims, 1 Drawing Sheet

ANTIMICROBIAL WOUND DRESSING AND SKIN FIXATOR FOR ORTHOPEDIC PINS

The present invention is directed to a device which serves as an antimicrobial wound dressing, skin fixator and anchoring device for orthopedic pins.

BACKGROUND OF THE INVENTION

Orthopedic pins, which are normally used in medical practice to temporarily immobilize and/or suture fractured bones, cause a breach in the skin. This wound provides a path for normal skin microorganisms to invade along the pin wound tract into deeper tissues, thus threatening the therapy being utilized and the health of the patient. Moreover, the potential for antimicrobial infection along the pin tract is increased by the relative motion of the pin into and out of the wound, and by bacterial proliferation at the wound site. Moreover, tissues contacting the pin are in a state of chronic inflammation, thus impairing the normal defense mechanisms against the progressive bacterial infection.

Thus it is an object of the present invention to stabilize an orthopedic pin at the wound site.

It is a further object of the present invention to provide an antimicrobial wound dressing at the pin site which can protect the wound site from the environment.

It is a further object of the present invention to provide a device which can be used both to anchor a pin with respect to the wound site and serve as a wound dressing, but which is disposable and readily replaced as needed without removing the pin or without undo disruption at the wound site.

These and other objects will be apparent from the following description and from the practice of the invention.

SUMMARY OF THE INVENTION

The present invention is directed to an antimicrobial orthopedic pin percutaneous protection kit. The kit comprises a shield comprising a central elastomeric collar having a longitudinal orifice and having one end of the collar substantially orthogonally disposed to an elastomeric, porous, peripheral flange, the flange extending around the end of the collar, with a radial slit extending through the collar and flange from the longitudinal orifice of the collar to the outer edge of the flange to provide a lateral insertion route for an orthopedic pin into the collar. The shield is adapted with means for securing the collar around an orthopedic pin to prevent longitudinal motion of the pin through the collar. The kit also comprises an absorbent patch containing an antimicrobial agent, centrally attached to a porous pad, the pad and patch having a pressure-sensitive adhesive coating on the exposed surface of the patch and the surrounding surface of the pad. The maximum dimensions of the pad are such that when the pad is placed upon the skin of a patient the superimposition of the shield upon the pad prevents contact of the flange of the shield upon the skin of patient. The patch and pad have a radial slit extending from a central point of the pad and patch to the outer edges of the pad and patch to provide a lateral insertion route of an orthopedic pin and to the pad and patch.

DESCRIPTION OF THE PREFERRED EMBODIMENTS

Figure 1:
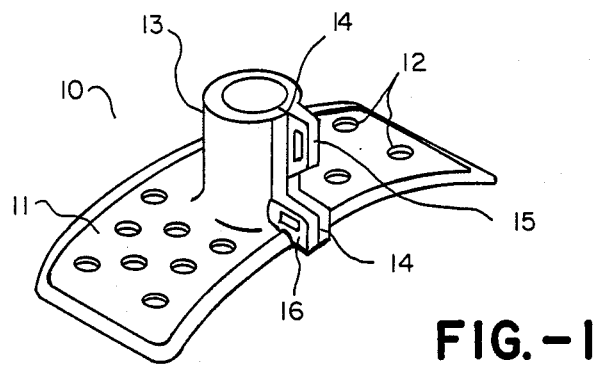
FIG. 1 is an exploded perspective view of one embodiment of the present invention showing a shield and pad/patch combination.

Referring to FIG. 1, an orthopedic pin shield 10 formed of an elastomeric material such as polyurethane, formed for example by conventional vacuum formation, injection molding or other means, is sterilizable and compatible with medication and body tissues. The shield 10 comprises a porous elastomeric peripheral flange 11 which is made porous by ventilation holes 12 and/or micropores (not shown) of sufficient size to allow the passage of moisture therethrough. Flange 11 may be flat, or have a slight curvature, as shown, to conform to skin surfaces. Co-formed or separately made and later attached, with the flange 11 is a central collar 13 orthogonally projecting above the plane of the flange 11. A radial slit 14 communicating the interior of collar 13 with the outer edge of flange 11 allows the insertion of an orthopedic pin into the collar 13 from a lateral direction. Eyelet 15 is co-formed or separately formed and later attached to, the exterior surface of the collar 13. Additional eyelets 16 are located on the flange 11 on either side of the radial slit 14.

The other component of the kit according to the present invention is an absorbent patch 18 centrally attached to a pad 17. The exposed surface of the pad 17 contains a pressure-sensitive adhesive for the attachment of the pad 17 to the skin of a patient, which serves in part to hold the patch 18 in close contact with the wound site formed by the orthopedic pin (not shown). A radial slit 19 communicates an interior orifice 20 of the pad 17 and a central point of patch 18, respectively, with the outer edges to allow the insertion of the pin into the orifice 20 and patch 18 from a lateral direction. It will be appreciated that orifice 20 may be of any desired dimension to accommodate different sized pins.

Figure 2:
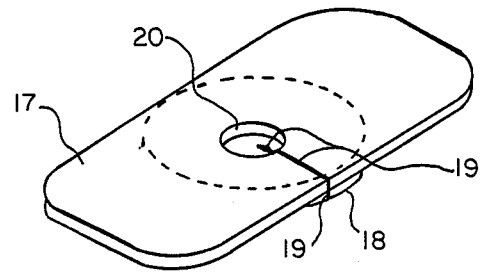
FIG. 2 is a partial cross-sectional of the pad and patch shown in FIG. 1.
Figure 2:
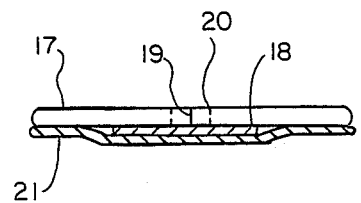

Referring to FIG. 2 there is shown a partial cross-sectional view of the pad and patch shown in FIG. 1. The cross-sectional view shows the additional feature of the removable tab 21 (shown in section) which covers the lower adhesive surface of the pad 17 (shown in section) for storage prior to use. The tab 21 may be made of any convenient material, such as paper or plastic. The tab (or tabs) is removed prior to the use of the pad 17 and patch 18.

During use, the tab 21 is removed from the pad 17 and patch 18 and the adhesive surface is placed onto the skin of a patient with the orthopedic pin extending through the orifice 20 and patch 18. Both the pad 17 and patch 18 are sufficiently porous to allow the passage of moisture therethrough. For use the shield 10 is placed over the pad 17 with the orthopedic pin (not shown) being inserted into the collar 13. The shield 10 is aligned with the pad 17 for the purpose, in part, of avoiding any abrasive effect of the flange 11 on the skin of the patient. The collar 13 is then tightened around the orthopedic pin (not shown) by inserting a suture or other suitable tying means (not shown) through the eyelets 15 and 16. The eyelets 16 are secured together by tying a knot to maintain closure of the radial slit 14, and the collar 13 is secured tightly around the orthopedic pin by tying a knot through eyelet 15 around the circumferential diameter of the collar 13.

The antimicrobial material contained in patch 18 may be any available antimicrobial agent such as chlorhexidene or an antimicrobial silver salt. In one particularly preferred embodiment the patch 18 is made of collagen and antimicrobial agent will be absorbed therein. The collagen will serve as an antimicrobial drug reservoir whereby the antimicrobial drug will be released gradually, thus providing a long-acting antimicrobial surface at the wound site.

In one modification the pad 17, flange 11 and/or interior of collar 13 may be impregnated with an antimicrobial agent to further reduce the risks of infection at the wound site. This is advantageous because incidental axial movement of the orthopedic pin through the collar 13 would result in a squeegee effect whereby bacteria are wiped off the orthopedic pin surface as it passes through the collar and into the tissues, and the antimicrobial agent is wiped over the orthopedic pin to further deter infection.

In a particularly preferred embodiment, the pad 17 and patch 18 may be used alone, without shield 10, in instances where pressure upon the skin and wound site caused by the immobilized shield 10 upon the orthopedic pin needs to be avoided. By using the patch 17 and pad 18 alone, minimal pressure is exerted upon the wound site and the orifice 20 serves to provide a squeegee effect whereby bacteria are wiped off the orthopedic pin surface as it passes through the orifice and into the tissues and antimicrobial agent is wiped over the orthopedic pin to further deter infection. If it is to be used without the shield 10, the patch 17 may be fabricated with an integral collar (not shown) centrally disposed thereon, and an eyelet similar to collar 13 and eyelet 15. In such a configuration the collar may also be impregnated with an antimicrobial agent.

The orthopedic pin kit according to the present invention may be used with any type of percutaneous device, particularly with bone fixation pins.

Having described the preferred embodiments of the present invention, it will be apparent to those skilled in the art that various modifications and variations may be made within the spirit and scope of the invention. The present invention is not to be limited except by the scope of the following claims.

What is claimed is:

1. An antimicrobial orthopedic pin percutaneous protection kit comprising a shield comprising a central elastomeric collar having a longitudinal orifice and having one end of said collar orthogonally disposed to an elastomeric, porous, peripheral flange, said flange extending around said end of said collar; and an absorbent patch containing an antimicrobial agent wherein said patch is centrally attached to a porous pad, said pad having a pressure-sensitive adhesive coating on the exposed surface thereof; the maximum dimensions of said pad being such that when said pad is placed upon the skin of a patient the superimposition of said shield upon said pad prevents contact of said flange upon the skin of said patient;

wherein a first radial slit extends through said collar and flange from said longitudinal orifice of said collar to the circumferential edge of said flange to provide a lateral insertion route of an orthopedic pin into said collar;

and a second radial slit extends from a central point of said pad and patch to the respective circumferential edges of said pad and said patch to provide a lateral insertion route of said orthopedic pin into said central point;

said shield adapted with means for securing said collar around said orthopedic pin to prevent longitudinal motion of said pin through said collar.

2. A kit according to claim 1 wherein said means for securing said pin comprises eyelets on the exterior surface of said collar and flange for accommodating tying means tightenable upon said collar.

3. A kit according to claim 1 further comprising one or more tabs, removably adherent to and at least cofacially coextensive with said adhesive coating.

4. A kit according to claim 1 wherein said absorbent patch comprises collagen.

5. A kit according to claim 4 wherein said collagen serves as an antimicrobial drug reservoir.

6. A kit according to claim 1 wherein said flange and pad are microporous to enhance vapor transmission therethrough.

7. A kit according to claim 1 wherein said antimicrobial agent is selected from the group consisting of chlorhexidene and silver salts.

8. A kit according to claim 7 wherein said antimicrobial agent comprises chlorhexidene.

9. A kit according to claim 1 wherein said flange and collar are impregnated with an antimicrobial agent.

10. A kit according to claim 1 wherein said pad is impregnated with an antimicrobial agent.

11. An antimicrobial orthopedic pin percutaneous protection shield comprising
an absorbent patch comprising collagen and containing an antimicrobial agent, wherein one of the surfaces of said patch is centrally and cofacially attached to a surface of a porous pad wherein a radial slit extends from a central point through said patch and said pad to the respective circumferential edges of said patch and said pad to provide a lateral insertion route of an orthopedic pin into said central point, said pad and said patch having a pressure-sensitive adhesive coating on at least one surface of said patch and on the exposed portion of said surface of said pad.

12. A shield according to claim 12 wherein said collagen serves as an antimicrobial drug reservoir.

13. An antimicrobial orthopedic pin percutaneous protection shield comprising
an absorbent patch containing an antimicrobial agent, wherein one of the surfaces of said patch is centrally and cofacially attached to a surface of a microporous pad wherein a radial slit extends from a central point through said patch and said pad to the respective circumferential edges of said patch and said pad to provide a lateral insertion route of an orthopedic pin into said central point, said pad and said patch having a pressure-sensitive adhesive coating on at least one surface of said patch and on the exposed portion of said surface of said pad.

14. An antimicrobial orthopedic pin percutaneous protection device comprising
an absorbent patch containing an antimicrobial agent, wherein said patch is cofacially and centrally attached to a porous pad, said pad having a pressure-sensitive adhesive coating on the exposed surface thereof, wherein a radial slit extends from a central point of said pad and said patch to the respective circumferential edges of said pad and said patch to provide a lateral insertion route of said orthopedic pin into said central point; and further comprising a central elastomeric collar disposed at said central point, said collar adapted with means for securing said collar around said orthopedic pin to prevent longitudinal motion of said pin through said collar; said means comprising an eyelet on the exterior surface of said collar for accommodating tying means tightenable upon said collar.

* * * * *

UNITED STATES PATENT AND TRADEMARK OFFICE
CERTIFICATE OF CORRECTION

PATENT NO. : 4,856,504
DATED : August 15, 1989
INVENTOR(S) : Yamamoto et al.

It is certified that error appears in the above—identified patent and that said Letters Patent is hereby corrected as shown below:

Column 4
Claim 12, line 44, please change "12" to read --11--.

Signed and Sealed this

Nineteenth Day of November, 1991

Attest:

HARRY F. MANBECK, JR.

*Attesting Officer*          Commissioner of Patents and Trademarks

UNITED STATES PATENT AND TRADEMARK OFFICE
CERTIFICATE OF CORRECTION

PATENT NO. : 4,856,504

DATED : August 15, 1989

INVENTOR(S) : Ronald Yamamoto, et al.

It is certified that error appears in the above-indentified patent and that said Letters Patent is hereby corrected as shown below:

On the title page, item (21) " 108,515" should read--108,518--.

Signed and Sealed this

Fifth Day of April, 1994

*Attest:*

BRUCE LEHMAN

*Attesting Officer*   *Commissioner of Patents and Trademarks*